United States Patent
Marx et al.

(10) Patent No.: US 7,501,232 B2
(45) Date of Patent: Mar. 10, 2009

(54) METHOD FOR CELL SELECTION

(75) Inventors: Uwe Marx, Berlin (DE); Christian D. Demmler, Berlin (DE); Christoph Giese, Berlin (DE)

(73) Assignee: Probiogen AG, Berlin (DE)

( * ) Notice: Subject to any disclaimer, the term of this patent is extended or adjusted under 35 U.S.C. 154(b) by 618 days.

(21) Appl. No.: 10/844,252

(22) Filed: May 12, 2004

(65) Prior Publication Data

US 2005/0032127 A1  Feb. 10, 2005

(30) Foreign Application Priority Data

May 12, 2003  (EP)  .................................. 03010582

(51) Int. Cl.
*A01N 1/02*  (2006.01)

(52) U.S. Cl. ................. 435/2; 435/3; 435/7.1; 435/7.2; 435/173.7; 435/173.8; 435/40.51; 435/373; 435/374; 435/383; 435/285.2; 435/286.2; 435/286.5; 435/287.2; 435/288.5; 436/15; 436/63; 436/149; 436/164; 436/172

(58) Field of Classification Search .................. 435/1.1, 435/2, 3, 7.1, 7.2, 366, 40.51, 372–374, 383, 435/285.2, 286.2, 287.2, 288.5, 286.5, 514, 435/516, 546, 15, 164, 172, 63, 149; 436/514, 436/516, 546, 149, 15, 63, 164, 172

See application file for complete search history.

(56) References Cited

U.S. PATENT DOCUMENTS 6,540,895 B1 *  4/2003  Spence et al. ............... 204/450

FOREIGN PATENT DOCUMENTS

| WO | WO 01/32844 | 5/2001 |
| WO | WO 03/072699 | 9/2003 |
| WO | WO 03/072699 A2 * | 9/2003 |

OTHER PUBLICATIONS

Huang et al., Dielectrophoretic Cell Separation and Gene Expression Profiling on Microelectronic Chip Arrays, Analytical Chemistry 74 (14): 3362-3371 (Jul 15, 2002).*

Fuhr et al., Cell manipulation and cultivation under AC electric field influence in hughly conductive culture media, Biochimica et Biophysica Acta 353-360 (1994).*

Huang Ying et al. "Dielectrophoretic cell separation and gene expression profiling on microelectronic chip arrays." Analytical Chem. (2002) 74(14):3362-3371.

Wang et al. Cell separation by dielectrophoretic filed-flow-fractionation. Analytical Chem, (2000) 72(2):832-839.

* cited by examiner

*Primary Examiner*—Gailene R Gabel
(74) *Attorney, Agent, or Firm*—Ballard Spahr Andrews & Ingersoll, LLP

(57) ABSTRACT

The invention relates to a method for the non-invasive selection of single living cells under gentle conditions from mixtures of cells or cell cultures with respect to a specific production performance. To this end, the concentration of substances produced by the individual cells which become enriched at the cell membrane, such as reporter gene products (GFP) or specifically secreted products, such as antibodies, is determined by fluorescence-microscopic detection methods.

24 Claims, 6 Drawing Sheets

(A)  (B)  (C)  (D)

(A)    (B)    (C)    (D)

METHOD FOR CELL SELECTION

CROSS REFERENCE TO RELATED APPLICATIONS

The present application claims priority to European Application No. 03010582.9, filed May 12, 2003, which application is incorporated herein fully by this reference.

The invention relates to a method for the non-invasive selection of single living cells under gentle conditions from mixtures of cells or cell cultures with respect to a specific production performance. To this end, the concentration of substances produced by the individual cells which become enriched at the cell membrane, such as reporter gene products (GFP) or specifically secreted products, such as antibodies, is determined by fluorescence-microscopic detection methods.

BACKGROUND OF THE INVENTION

Flow cytometry in combination with selective cell sorting (FACS: Fluorescence Activated Cell Sorting) is a method which became established more than 20 years ago. It allows the rapid screening and sorting of a large number of cells (sorting rates of up to 2000 cells/s). However, it has been predominantly used in the analytical field (medical diagnostics). Becton Dickinson, Beckman Coulter or Cytomation offer appropriate technological equipment with cell sorting options which enable an at least antiseptic operation. A sterile or even GMP-conforming process cannot be ensured and seems to be very difficult to realize also in the future. To ensure a high sample throughput, a rapidly flowing fluidic system is required. The shear forces occurring during the passage of the cells represent a massive impairment of cellular functions and clearly reduce viability in preparative applications and may result in long-lasting changes of the cellular morphology, growth and productivity or other specific functions. In addition, the selected cells are pooled; a safe collection of single cells does not appear to be realizable technically for these sample throughputs.

Cells can be cultured while embedded in viscous media (semisolid matrix). By a secretion assay, a secreted product can be stably precipitated in a stable cloud around the cell by means of a fluorescence-coupled detection system. This cloud, which exhibits a stronger fluorescence than that of the background can be utilized for a rough evaluation of high producers. In a second step, cells identified as high producers by an image analysis can be removed manually or automatically through a micromanipulator-operated glass capillary and cultured further (DE-A-10209788). However, this method has drawbacks relating to detection sensitivity and a limited sample throughput due to a low automatization potential.

The US-American company One-Cell Systems Inc. trades a special method for the FACS-supported sorting of gel microdrops by FACS. This ensures an at least cell-saving selection process, which is combined with the high sorting speed of FACS technology. Cells are included in gel microdrops having diameters of 20-100 µm. There, they secrete their product, which is bound to a special agarose matrix through a product-specific capture antibody. In a second step, the bound product is detected by a fluorescence-labeled product-specific antibody, and the number of cells is simultaneously determined due to the localization (FIG. 1b). The fluorescence signal can be used for sorting the drops by means of FACS technology. Subsequently, the matrix is dissolved again, and the cells are suspended.

In addition, there is also a possibility of isolating cells having a specific secretory activity by immunomagnetic separation (Miltenyi, Dynal Biotech, Polysciences). However, this method has the disadvantage that it does not allow for a quantification of the secretion performance and does not exhibit single cell specificity.

Therefore, there has still been a need for a method which can improve particular properties of a cell culture, such as the production performance, by a well-aimed selection of single cells and their subsequent further culturing in said cell culture.

SUMMARY OF THE INVENTION

It has now been found that the product concentration and thus the synthetic performance of a cell can be determined by the quantification of the expressed products of the cell adhering to the cell membrane and of fluorescent products in the cell or cell membrane, e.g., by fluorescence-microscopic methods. Thus, the invention relates to a method for the selection of cells producing a specific product from a mixture of cells, which comprise the quantitative determination and evaluation of the individual production performance of a single fixated cell by means of the specific product enriched in or on it. The method is suitable to be performed on the intact viable cell which remains viable and can afterwards be cultivated.

The method according to the invention enables both the determination of the relative synthetic performance (embodiment A) and, due to a fluorescence-spectroscopic measurement, an exact and absolute determination of concentration (embodiment B) from which an absolute specific production performance can be derived by a standardizable and normalizable experimental set-up.

Figure 4:
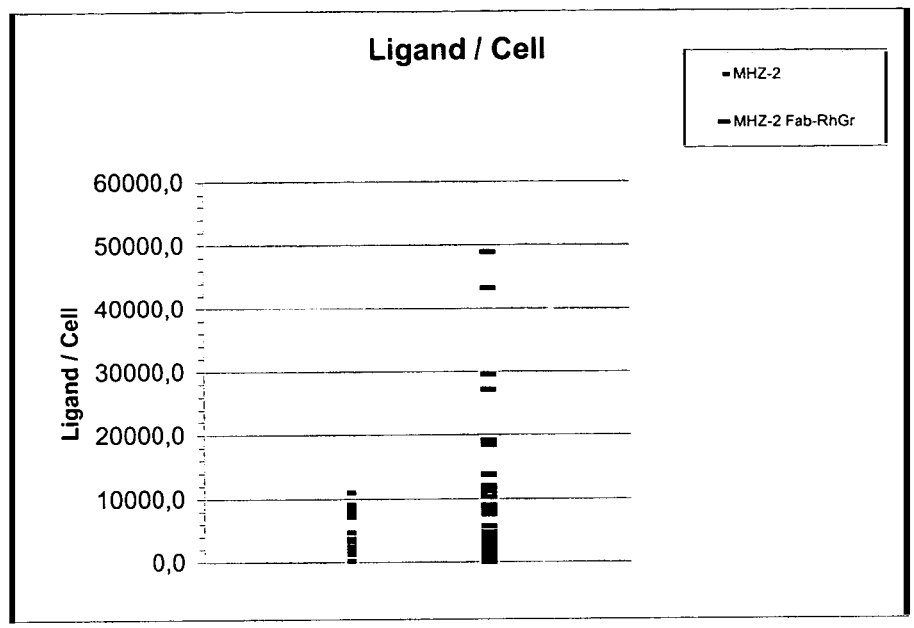
Figure 4:
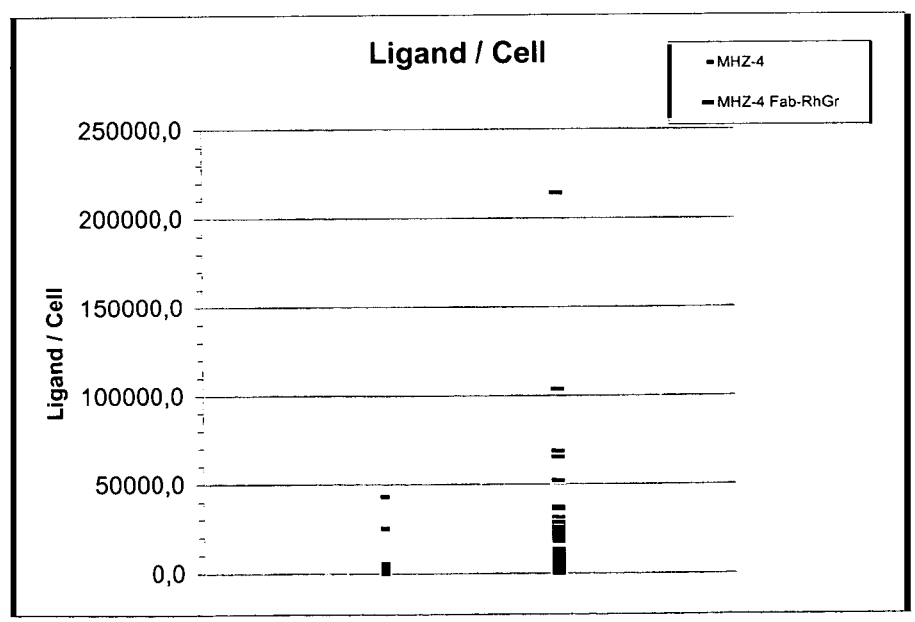

FIG. 4 shows comparative measurements of two hybridoma clones, MHZ-2 (FIG. 4A) and MHZ-4 (FIG. 4B). The right-hand data series respectively show the distribution of amounts of product molecules for 50 measured cells, the left-hand data series show signals of non-labeled cells (background signals).

Figure 5A:
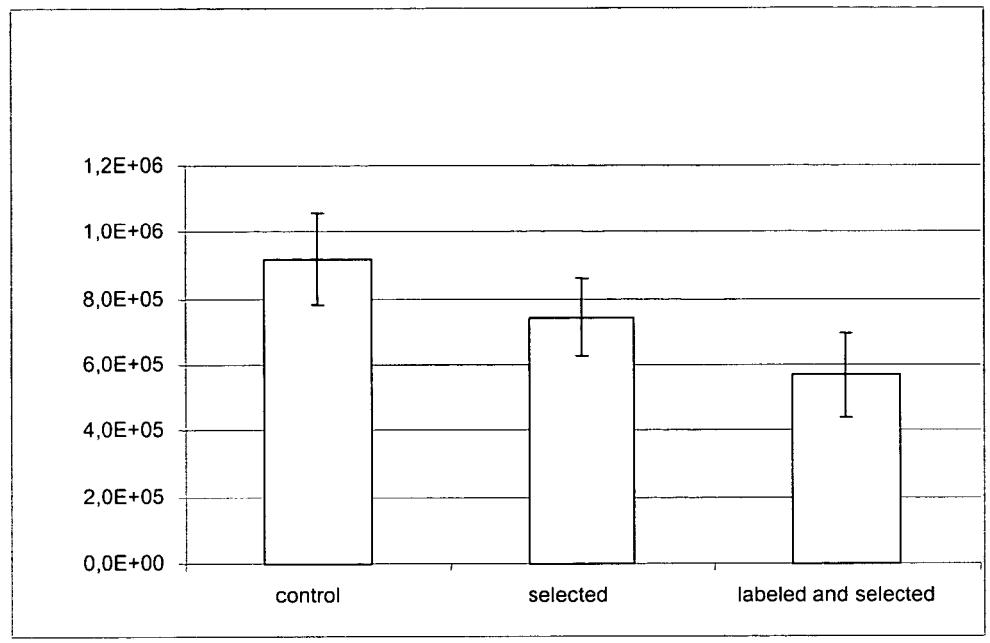
Figure 5B:
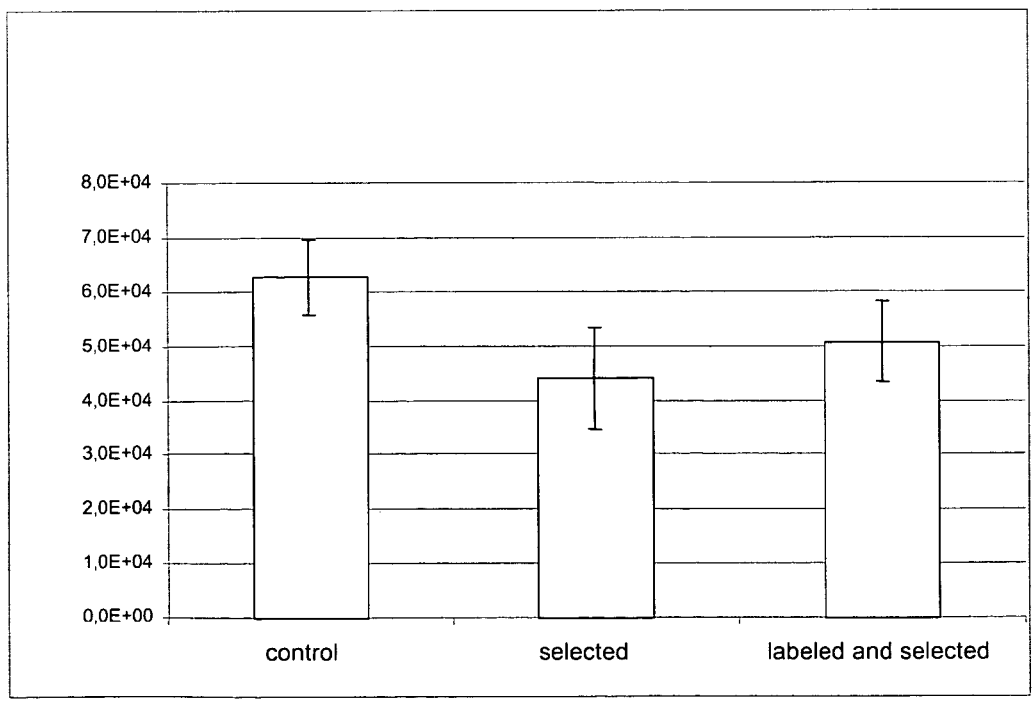

FIG. 5: Culture of assay treated and selected cells compared to culture of only selected cells and control (whether assay treated nor selected) for 168 h under standard culture conditions as described (n=3). As shown in FIG. 5A, using 1,000 cell per ml a reduced outgrow of about one third was observed for fully treated cells. As shown in FIG. 5B, using 100 cells per ml a reduced vital cell concentration of $5\times10^5$ compared to $6\times10^5$ for untreated control was observed.

Figure 6:
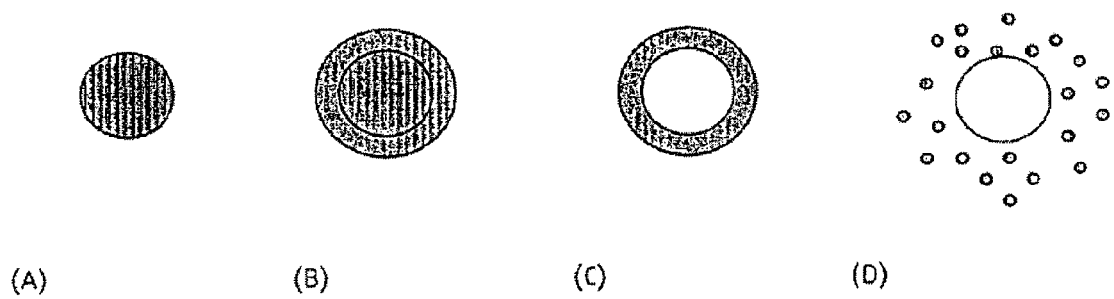

FIG. 6: Fluorescence phenomena with different cellular localizations: only intracellular (A), intracellular and membrane-bound (B), only membrane bound (C), and pericellular (D).

DETAILED DESCRIPTION OF THE INVENTION

In the method according to the invention, the product can be localized in the cell, in the cell membrane or on the cell membrane (secreted). These different localizations of the product are illustrated in more detail in the sketch of FIG. 6.

Fluorescence phenomena with different cellular localizations: only intracellular (A), intracellular and membrane-bound (B), only membrane-bound (C), and pericellular (D).

The determination of the production performance can be effected by optical microscopy or by fluorescence-spectroscopic methods. An important aspect of the method according to the invention is the fact that the determination is made while the cell is fixated (hereinafter referred to as "immobilized"). Then, from the detected production performance, a classification can be immediately made through defined threshold values into cells to be selected and cells not to be selected.

By the method according to the invention, the product selected from proteins, glycosides and derivatives and combination products from these classes of substances etc. can be determined. The products are preferably selected from proteins and peptides, such as antibodies, antibody fragments, cytokines etc., as well as glycosylated derivatives of proteins and peptides or derivatives provided with detectable markers or with fluorescent domains. In the method according to the invention, the product can be expressed by a primary cell or as a consequence of a manipulation of the cell, i.e., primary cells (i.e., non-manipulated cells) or transformants can be employed. In the method according to the invention, the product may be directly detectable and, in particular, may have a domain which can be detected by fluorescence microscopy or spectroscopy, or may be indirectly detectable by complexing with a detector compound, especially a fluorescence-labeled antibody.

The method according to the invention may further comprise a selecting step in which the mixture of cells is preferably guided through a microfluidic system. In this case, it is preferred that the individual cells are identified as such from a flowing movement in the microfluidic system, selectively stopped and measured by continuously monitoring their secretion performance. It is particularly preferred to effect the immobilization (fixation) of the cell in a contactless manner by an electrostatic field cage (e.g., by negative dielectrophoresis).

In a further preferred embodiment of the method according to the invention, the product itself may be fluorescent and its concentration derived from the measured fluorescence signal. Alternatively, the product may be quantified by complex formation through receptor-ligand interaction, the complex formation being detectable by fluorescence spectroscopy and allowing a determination of the product concentration. The complex formation is preferably effected by an antigen-antibody interaction which can be detected by fluorescence spectroscopy and allows determination of the relative product concentration.

The absolute specific production performance (embodiment B of the invention) can then be determined by adjusting the relative product concentration with the results obtained in a standardized set up. The cells selected in the method according to the invention can be selectively separated from the sample stream by deviation into a branching channel and collected in a suitable culture system. This deviating into a branching channel is preferably effected by opening electrostatic gates/sluices. The deviation of the (high producing) cells is effected by setting a specific threshold value (which may vary depending on cell type expression capacity etc. and is to be determined by the skilled artisan). The fact that the collection of the selected cells can be effected in a sterile manner is a remarkable feature of the method according to the invention.

The culturing of the cells is preferably effected in a culture system which is optimized for the culturing of single cells or a few cells (for mammal cells, e.g., human, murine and bovine cells (primary, transformed and/or immortalized)), being optimized by supplementing, selected conditioning or special formulation. The culture system may be miniaturized, which means that the culture volume is reduced. Further, the culture medium may be supported by using a biogenic or artificial extracellular matrix.

The method according to the invention is particularly suitable for the identification and selection of single cells having a high production performance or secretory performance and/or optimization of production processes based on cell cultures. The selected (separated) single cells obtained by the method of the invention show an excellent outgrow behaviour comparable to the starting cells.

The invention is further illustrated by the following Examples which are not, however, intended to limit the scope of the invention.

EXAMPLES

Materials and Methods

Assay: The preparation of the cells for the Cytocon system in combination with an FCS+plus measurement was effected by the following steps:

Remove cell supernatant and determine the cell count (viability) with the Coulter Z2;

add $1\times10^6$ viable cells to a 15 ml Falcon+10 ml PBS and centrifuge off at 100×g for 10 min;

discard supernatant except for a minimum residual volume and resuspend pellet in 5 µl RhGr-Fab and incubate at 37° C. for 30 min;

add 10 ml of PBS, resuspend and centrifuge off at 100×g for 10 min;

remove supernatant, take up pellet in 2 ml of Cytocon buffer II (1:4) and fill injection syringe (100 µl).

Cell lines: For the selection experiments within the scope of a feasibility study, two cell lines were chosen which are of importance in production processes of Applicant and therefore have been characterized comprehensively (MHZ-2; MHZ-4). For measurements by flow cytometry, the cell line MHZ-3 was employed. The MHZ-cell lines used in the selection processes described below are hybridoma cell lines of mouse origin. They were optimized by repeated subcloning and well characterized for production rates and clonal stability. They are suitable for production of a specific monoclonal antibody in industrial scale. The secreted antibody is a mouse monoclonal immuneglobuline of the IgG type. In a classical maintenance culture ($10^3$-$10^6$ cells/ml) for MHZ-2, the production performances are 5-50 ng per 1000 cells per day. This corresponds to a specific IgG production rate of 60-600 molecules per cell per s.

In a cell line culture, productivities for the cell clones employed were estimated and based on 1-4·$10^7$ cells/ml of culture volume. The product concentrations were determined by anti-mouse Fcγ-specific ELISA.

| | |
|---|---|
| MHZ-2 | 40-100 µg/day |
| MHZ-4 | 400-800 µg/day |

The productivity of MHZ-4 is higher by a factor of up to 10 as compared to that of MHZ-2.

Detection system: Within the scope of the feasibility study, various detection systems for assay development were tested in comprehensive measuring series. These were commercially available antibody conjugates for immunofluorescence microscopy (IgG-texas red), bacterial recombinant protein A and protein G, and a cleavage product of an IgG antibody, a f(ab) preparation.

Example 1

Quantification of the Secretion Performance by Insight Scans by Means of the Precipitate Shell The quantification of the secretion performance was accomplished by measuring the precipitate shell which forms around a cell over a defined incubation period. (Together with product molecules, detection molecules form a precipitate shell which surrounds the cell and whose intensity corresponds to the amount of secreted product. The measuring of the cell-bound fluorescence phenomenon permits a determination of the cell-specific production rate.) The determination of the product concentration was performed, in terms of measurement technology, either by fluorescence spectroscopy by means of insight technique, but also by fluorescence microscopy through an imaging method. The measuring signals of the fluorescent precipitate shell were essentially higher and could be detected without difficulty with the tested detection systems. This imaging method provided for a substantial speeding-up of the selection process and a simpler and safer evaluation method. However, it did not permit the determination of absolute concentration, but merely a relative classification of cells due to the evaluation of the image or object brightness.

Figure 1:
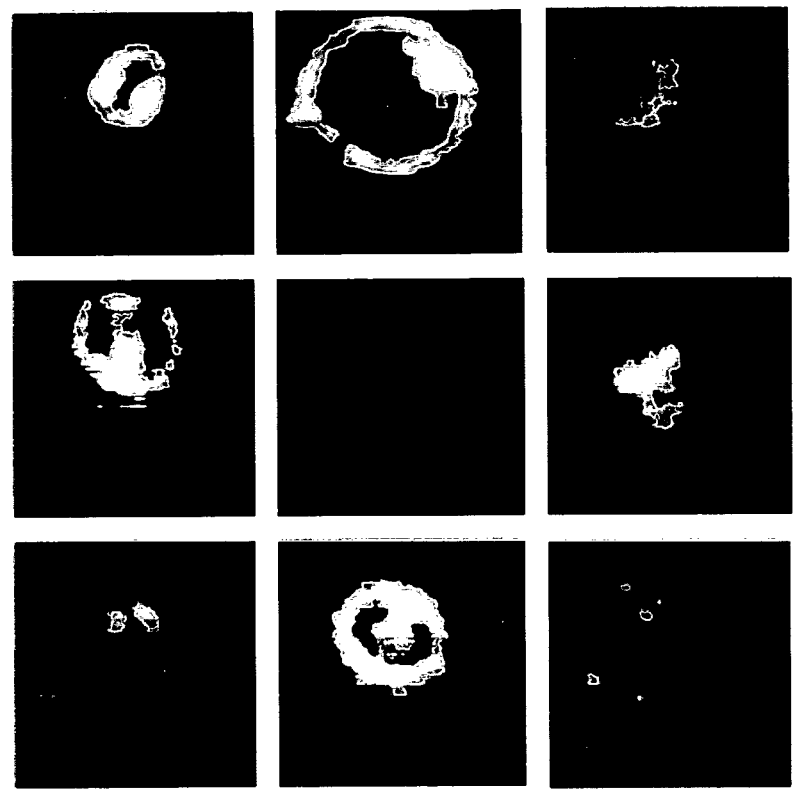
FIG. 1 shows a selection of insight cell scans of the cell clone MHZ-2 (FIG. 1A) and MHZ-4 (FIG. 1B).
Figure 1:
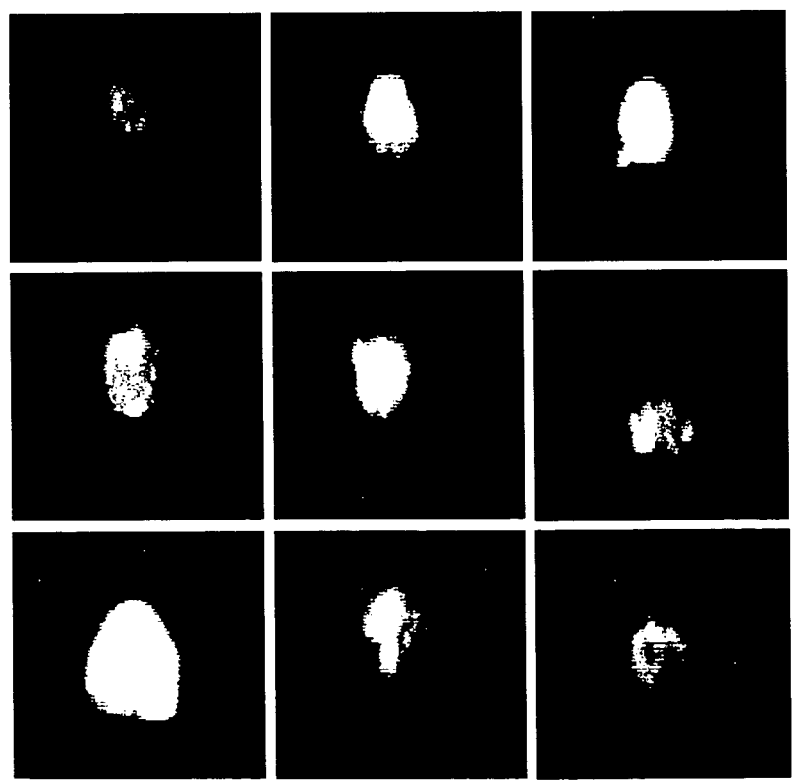
Figure 2:
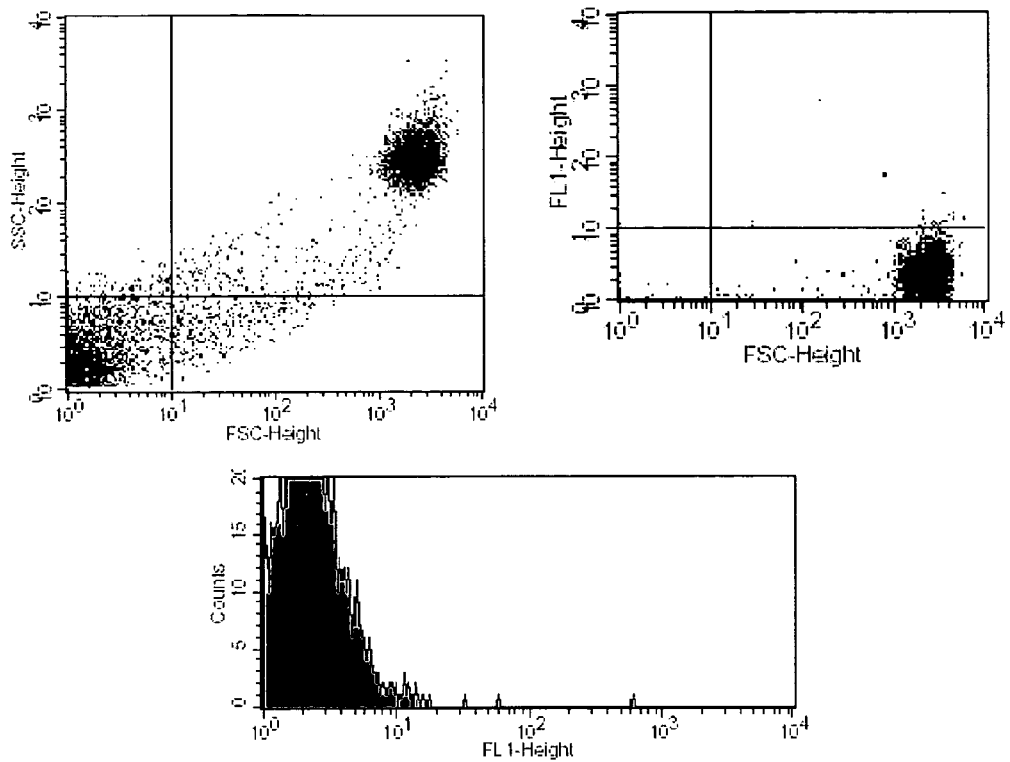
FIG. 2A: Comparative measurement of envelope formation by means of flow cytometry, measuring the fluorescence background of MHZ-3; FACS measurement of non-labeled cells (MHZ-3).
FIG. 2B: Measurement of the product-specific fluorescence (MHZ-3); FACS measurement of product-specifically labeled cells (MHZ-3); in each case secretion assay with anti-mouse IgG-fab-RhGr, wherein:
top left: dot-plot particle granularity vs. particle size
top right: dot-plot autofluorescence vs. particle size
bottom: histogram of fluorescence intensity (blue: labeled; red: non-labeled)
FSC height: relative particle size (forward scatter)
SSC height: relative granularity of the particles (sideward scatter)
FL1 height: fluorescence (channel 1) at 530 nm (BP 30) (excitation: 488/685 nm)
FIG. 2C: Measurement of the fluorescence caused by non-specific binding events FACS measurement of non-specifically labeled cells (MHZ-3) (secretion assay with anti-sheep IgG-texas red)
Histogram of fluorescence intensity (blue: labeled; red: non-labeled)
FL2 height: fluorescence (channel 2) at 585 nm (BP 42) (excitation: 488/685 nm)
Figure 2:
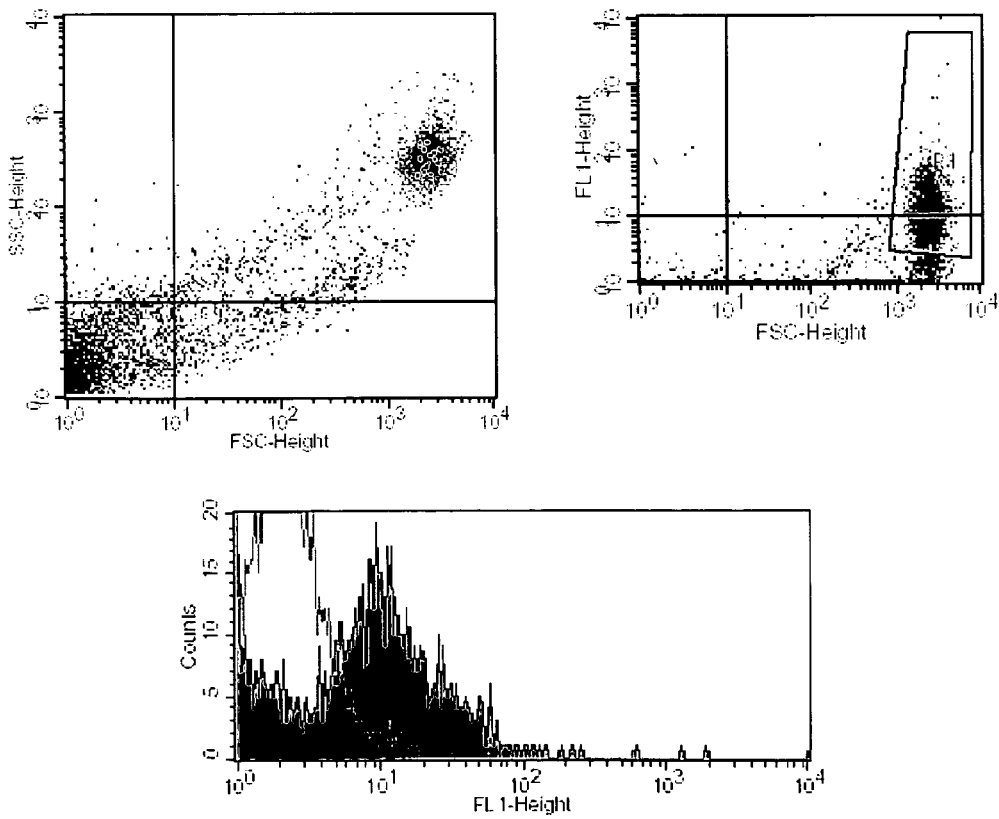
Figure 2:
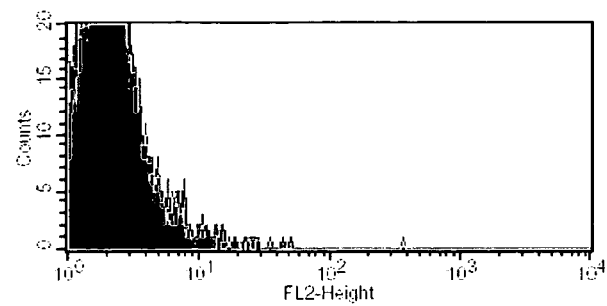
Figure 3:
FIG. 3 shows paraformaldehyde-fixed cell preparations recorded with a confocal laser scanning microscope (568/590 nm) after performance of the secretion assay and superimposed on a transmission optical microscope image.

The cells stained according to the standardized assay protocol (2 hybridoma cell clones) showed a product-specific fluorescence in the form of a shell. The intensity of shell formation was proportional to the actual secretion performance (measurement of the secreted product in the culture supernatant of different clones). With the progress of incubation time, the shell formation increased. After the stopping of the incubation time by the washing process, it remained on a constant level over 80 min. After a secretion assay, the cells showed a clear and individually distinguishable fluorescence phenomenon. It could be localized predominantly as being extracellular and membrane-bound. However, it could also appear two-dimensionally or granularly in the cytoplasm, as with MHZ-4. The specific shell formation and its differential fluorescence were detected in insight scans (FIGS. 1A and B), in an examination by flow cytometry (FACS; see FIG. 2A-C) and in a confocal laser scanning microscope (LSM; see FIG. 3). The cells showed an intrinsic fluorescence. This could be distinguished from the specific fluorescence by setting a threshold value.

In the field cage, artifacts were observed which had a granular appearance. This was due to the nature of the negative dielectrophoresis in the field cage. All kinds of particles were enriched in the cage zone (e.g., also stained cell debris and probe aggregates) and adhered to the surface of the cell. This did not interfere with the measuring method and had no influence on the viability of the cells.

Data analysis: For MHZ-2 and MHZ-4, a background noise of up to 10,000 and 50,000 ligands/cell, respectively, was obtained from the intrinsic fluorescence of the cells. Secretion-specific signals ranged from 10,000 to 50,000 and 50,000 to 200,000 ligands/cell, respectively (see FIGS. 4A and 4B). A high producer selection was effected for MHZ-2 at values of above 30,000 and for MHZ-4 at values of above 100,000 ligands/cell.

From ELISA comparative measurements of supernatants from the established culture of the two selected clones (anti-mouse Fcγ-specific), the following productivities were determined:

| | |
|---|---|
| MHZ-2 | 40-100 µg/day |
| MHZ-4 | 400-800 µg/day |

Accordingly, the productivity of MHZ-4 was higher than that of MHZ-2 almost by a factor of 10. This result was confirmed by the small number of cells measured here.

Example 2

Collection of Selected Cells and Detection of the Growing of Clones

To investigate the capability of subcultivation and the stability of enhanced productivity after selection process selected cell pools were held in long term culture. A mix of D-MEM/HAM's F-12 (1:1) supplemented with 10% (v/v) fetal calf serum (FCS) and conventional T-flasks were used for cell cultivation.

Outgrow Behaviour

Single cells selected according to the method of Example 1 were deposited under sterile conditions into 96 well plates. In repetitive experiments it was shown that single cells could be deposited into single wells of a 96 well plate in a culture volume of 50 µl with high accuracy.

The application of the secretion assay in combination with the single cell deposition was proven to be a mild treatment process. The outgrow behaviour of different treated cell populations was tested in various culture experiments. The outgrow of cells treated by the screening assay and/or selection process was compared to untreated cells in pools of 1,000 or 100 cells using a 24 well plate and a culture volume of 1 ml for 168 h (FIG. 5A, B).

Using 1,000 cell per ml a reduced outgrow of about one third was observed for fully treated cells. Using 100 cells per ml a reduced vital cell concentration of $5 \times 10^5$ compared to $6 \times 10^5$ for untreated control was observed.

Surprisingly, the treated cells showed an increased viability of 92% compared to 82% in untreated control after 300 h culture time. This culture (outgrow) experiment shows that the cells selected and deposited according to the method described above possess an outgrowing behaviour comparable to that of cells passaged with conventional pipetting methods. The outgrow experiments further show comparable initial lag-phases and cell number at the end of culture period.

Stability of enhanced productivity after selection process in long term cultivation: The cells were selected using a fluorescence activated cell sorting device (FACS, FACS Vantage, BD Bioscience). At first, a part of homogenous cell suspension MHZ-2 (labeled as described) was screened on the distribution of fluorescence intensity. The fluorescence intensities were distributed over two decades. A threshold (gate, P3) was defined on the 200 fold of lowest intensity. Cells of higher fluorescence intensity were sorted and pooled by the FACS sorter device. In two sessions 8,700 and 25,200 cells were prepared as "high producers" (FIG. 5). A part of the not selected "low producer" cells was cultivated as negative control.

Specific productivity was quantified by ELISA and cell enumeration in supernatants of culture aliquots after a short cultivation period of 7 days. At the end of the long term culture of 71 days (correlates to 44 and 47 cell doublings in reference culture) the specific productivity was quantified a second time. No increase in productivity of the expanded "high producer" cell pool was observed. The ratio of productivity between low and high producers was constant over culture period.

We claim:

1. A method for the selection of intact viable cells producing a specific product from a mixture of cells, comprising quantitatively determining and evaluating the individual production performance of a single fixated cell by means of the specific product enriched on it, said determination being performed on the fixated intact viable cell, wherein the fixation of the cell is effected in a contactless manner by an electrostatic field cage, and wherein quantitative determination is performed on the product that is localized on the cell membrane or that is localized outside but in close vicinity of the cell over a defined incubation period as a basis for selection of the intact viable cells.

2. The method of claim 1, wherein the determination of the production performance is effected by optical microscopy or by fluorescence spectroscopy.

3. The method of claim 1, wherein the determination is effected with fixation of the cell.

4. The method of claim 1, further comprising comparing production performance of cells to threshold values and immediately classifying the cells into cells to be selected and cells not to be selected.

5. The method of claim 1, wherein the product is selected from the group consisting of proteins, glycosides and derivatives and combination products from these classes of substances.

6. The method of claim 5 wherein the product is selected from the group consisting of proteins and peptides, as well as glycosylated derivatives of proteins and peptides and derivatives of proteins and peptides provided with detectable markers or with fluorescent domains.

7. The method of claim 6, wherein the product is selected from the group consisting of antibodies, antibody fragments and cytokines.

8. The method of claim 1, wherein the product is expressed by a primary cell or as a consequence of a manipulation of the cell.

9. The method of claim 1, wherein the product is directly detectable or is indirectly detectable by complexing with a detector compound.

10. The method of claim 9, wherein the product is directly detectable and has a domain which can be detected by fluorescence microscopy or spectroscopy.

11. The method of claim 9, wherein the detector compound is a fluorescence-labeled antibody.

12. The method of claim 9, wherein the complex formation occurs through receptor-ligand interaction and, the complex formation is detectable by fluorescence spectroscopy and allows a determination of the product concentration.

13. The method of claim 12, wherein said complex formation is effected by an antigen-antibody interaction which can be detected by fluorescence spectroscopy and allows determination of the product concentration.

14. The method of claim 1, wherein said method further comprises a selection step.

15. The method of claim 14, wherein in the selection step the mixture of cells is guided through a microfluidic system.

16. The method of claim 14, wherein in the selection step the individual cells are identified as such from a flowing movement in the microfluidic system, selectively stopped and measured by continuously monitoring their secretion performance.

17. The method of claim 1, wherein the product itself is fluorescent and its concentration can be derived from the measured fluorescence signal.

18. The method of claim 1, wherein the cells to be selected are selectively separated from the sample stream by deviation into a branching channel and collected in a suitable culture system.

19. The method of claim 18, wherein said deviating into a branching channel is effected by opening electrostatic gates/sluices.

20. The method of claim 18, wherein the collection of the selected cells is effected in a sterile manner.

21. The method of claim 18, wherein the culture system is optimized for the culturing of single cells or a few cells.

22. The method of claim 18, wherein the culture system is miniaturized and the culture volume is reduced.

23. The method of claim 18, wherein the culture system is optimized for the culturing of single cells or a few cells by supplementing, selected conditioning or special formulation.

24. The method of claim 18, wherein the culture system comprises culture medium and biogenic or artificial extracellular matrix.

* * * * *